United States Patent [19]

Ishii et al.

[11] 4,394,315
[45] Jul. 19, 1983

[54] METHOD FOR MANUFACTURING P- AND O-BENZOQUINONE DERIVATIVES

[75] Inventors: Fumio Ishii, Hino; Kenichi Kishi, Sagamihara, both of Japan

[73] Assignee: Konishiroku Photo Industry Co., Ltd., Japan

[21] Appl. No.: 229,061

[22] Filed: Jan. 28, 1981

[30] Foreign Application Priority Data

Jan. 31, 1980 [JP] Japan .................................. 55-10884

[51] Int. Cl.³ ...................... C07C 46/06; C07C 50/04; C07C 50/08; C07C 50/12; C07C 50/18
[52] U.S. Cl. .................................. 260/396 R; 260/369
[58] Field of Search .................. 260/396 R, 369, 383, 260/384, 396 K

[56] References Cited

U.S. PATENT DOCUMENTS 3,796,732 3/1974 Brenner ........................... 260/396 R
3,941,811 3/1976 Vignau ............................. 260/396 R

*Primary Examiner*—Vivian Garner
*Attorney, Agent, or Firm*—Finnegan, Henderson, Farabow, Garrett & Dunner

[57] ABSTRACT

A method for synthesizing p- or o-benzoquinone derivatives represented by formula III or IV

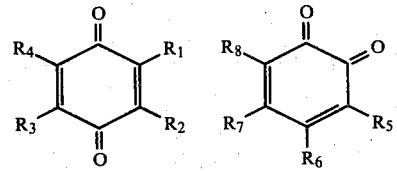

III          IV by oxidizing, with an aqueous hypohalite solution having a pH of from 8 to 10, a p- or o-hydroquinone derivative represented by formula I or II

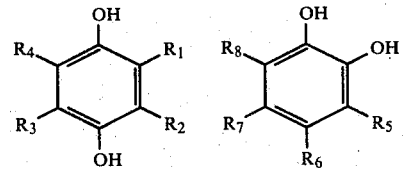

I          II

Oxidation is conducted at a temperature between −20° C. and 35° C., in the presence of a quaternary ammonium salt phase transfer catalyst.

6 Claims, No Drawings

METHOD FOR MANUFACTURING P- AND O-BENZOQUINONE DERIVATIVES

The present invention relates to a method for manufacturing p- or o-benzoquinone derivatives, which are useful as starting materials or final product in the field of, for example, medicament, dye or photographic material.

With respect to the syntheses of p- or o-benzoquinone derivatives, a number of synthesizing methods thereof have been known, for example, in the such literature as Houben-Weyl, "Methoden der Organishen Chemie" 7-3a, (Georg Thieme Verlag, Stuttgart) 1977; S. Patai, "The Chemistry of the Quinonoid Compounds" Part I, Interscience, New York, 1974 J. Cason, Org. Reactions 4, 305 (1948).

Inter alia, the methods for which corresponding p- or o-benzoquinone can be obtained by oxidizing p- or o-hydroquinone are being widely used owing to the facts that starting material is easily available, and that a high reaction yield is obtainable. As for the oxidizing agents for this purpose, a number of chemical compounds have been known, inter alia, the highly versatile oxidizing agents are heavy-metal salts, such as dichromate, chromate, permanganate and silver oxide. However, those are not suitable for use in quantity, because of the problems such as environmental pollution.

Many other oxidizing agents show their own peculiarity against hydroquinone as a starting material, therefore the sufficient yield has not been obtainable.

On the other hand, a number of studies are being made recently on heterogeneous reaction caused by making use of quaternary ammonium salt as a phase transfer catalyst, (hereinafter referred to as PTC.), which is one of the most effective means for making organic synthetic reaction. Concerning PTC, it is described in the literatures such as J. Dockx, Synthesis 441 (1973); E. Dehmlow, Angew. Chem., Int. Ed. Engl. 13, 170 (1974); W. P. Weder and G. W. Gokel, "Phase Transfer Catalysis in Organic Synthesis" Springer Verlag, Berlin, 1977; C. M. Starks and C. Liotta, "Phase Transfer Catalysis," Academic Press, New York 1978.

It has been disclosed in the U.S. Pat. No. 3,996,259 that a specific organic compound such as amine, amido, aldehyde, alcohol, can be oxidized by making use of aqueous hypohalite solution, in the presence of PTC in catalytic amount.

It is an object of the present invention to provide a method for synthesizing p- or o-benzoquinone derivative represented by the formula III or IV with high yields, in a short period of time, and safely or without environmental pollution.

Another object is to provide the method by making use of, as a starting material, p- or o-hydroquinone derivative.

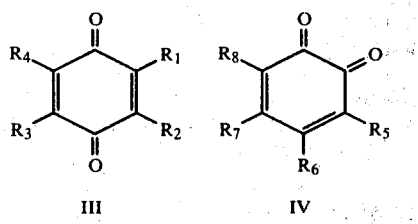

III   IV

In these formulae, $R_1$-$R_8$ represents hydrogen atom, alkyl group or aryl group, excepting the case that every $R_1$ to $R_4$ or $R_5$ to $R_8$ represent hydrogen atom; and $R_1$ and $R_2$, $R_3$ and $R_4$, $R_5$ and $R_6$ or $R_6$ and $R_7$ may form a 5 or 6-membered aromatic or aliphatic hydrocarbon ring.

As for alkyl group, it may also be of the straight chained or of the branched one, preferably having 1–32 carbon numbers, for example, a group of methyl, ethyl, n-butyl, t-butyl, n-hexyl, 2-ethyl hexyl, 3,5,5-trimethyl hexyl, 2,2-dimethyl pentyl, n-octyl, t-octyl, n-dodecyl, sec-dodecyl, n-hexadecyl, n-octadecyl, or eicosyl is given; as for aryl group, a group of phenyl or naphthyl is given. The alkyl or aryl group may have such a substituent as halogen, nitro, alkoxy, etc.

The new method of the present invention is to oxidize p- or o-hydroquinone derivative represented by the formula I or II by aqueous hypohalite in the presence of quaternary ammonium salt phase transfer catalyzer,

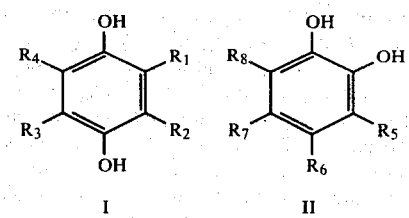

I   II wherein $R_1$ to $R_8$ have same meanings as defined in the formulae (III) and (IV).

Hypohalite to be used in the invention may be either sodium hypochlorite, sodium hypobromite or potassium hypobromite, and may also be one of the mixtures thereof. Hypohalite is prepared by saturating high concentration of aqueous solution of metal oxide which is caustic base, with halogen. The examples of the aqueous solution includes sodium hydroxide, potassium hydroxide, calcium hydroxide etc. The aqueous solution of hypohalite is such strong base that the pH value of it shows over 12. It is provided to the market.

The concentration of the aqueous hypohalite solution is not critical for the present invention. Commercially available that of 10 or 12% can be used as well as more dilute or more concentrated one. The value of pH may be adjusted with mineral acid such as hydrochloric acid, sulfuric acid etc.

Quaternary ammonium salts to be used as PTC are well known to the person skilled in the art. They are described, for example, in the literature of "Phase Transfer Catalysis" by M. Starks and C. Liotta, published by Academic Press, New York, 1978, and those may be formularized by the formula V:

$$R_9R_{10}R_{11}R_{12}N^+A^- \qquad (V)$$

(wherein, $R_9$ to $R_{12}$ represent hydrocarbon groups, such as those of alkyl, aryl, alkylaryl, arylalkyl, cycloalkyl; and, by taking two of $R_9$, $R_{10}$, $R_{11}$ or $R_{12}$ together, a five or six-membered heterocyclic ring). The heterocyclic rings may include oxygen or nitrogen other than quaternary nitrogen. The preferable ones as to $R_1$ to $R_4$ are of 10 to 30 carbon numbers in total.

$A^-$ represents a counter anion of quaternary ammonium cation, that is, anion of chlorine, bromine, fluorine, iodine, tosyl, acetyl, hydroxy or hydrogen sulfate, etc.

The typical chemical compounds to be used for the present invention out of the compunds formularized as in the general formula V are given as follows:

Chloride, bromide, fluoride, iodide, tosylate, acetylate, hydroxide or bisulfate of tetra-n-butyl ammonium, tri-n-butyl methyl ammonium, tetrahexyl ammonium, trioctyl methyl ammonium, hexadecyl triethyl ammonium, tridecyl methyl ammonium, tetrabenzyl ammonium, benzyl trimethyl ammonium, benzyl triethyl ammonium, benzyl tributyl ammonium, phenethyl trimethyl ammonium, N,N,N-trimethyl anilinium, N,N,N-triethyl anilinium, N,N-diethyl anilinium, trimethyl naphthyl ammonium, p-methyl phenyl trimethyl ammonium, N,N-dibutyl morpholium, or N-decyl thiazolium. When using 2.0 to 8.0 equivalents of hypohalite and 0.01 to 0.1 equivalent of quaternary ammonium salt with p- or o-hydroquinone derivative to be oxidized, the directing p- or o-benzoquinone derivative can be obtained with a good yield.

The preferable temperatures of the reaction are at $0°-35°$ C. with p-hydroquinone derivatives, and at $-20°-0°$ C. with o-hydroquinone derivatives.

It is preferable to make use of organic solvent to dissolve the starting material for the reaction, for example, hydrocarbon halogenide such as carbon tetrachloride, chloroform, and dichloromethane; aromatic hydrocarbon such as benzene and toluene; or fatty acid ester such as ethyl acetate and butyl acetate.

The typical examples are given in Formula I and Table 1, and Formula 2 and Table 2 representing the results obtained by using tetra-n-butyl ammonium sulfate as a PTC, sodium hypochloride as a hypohalogenite, and chloroform or dichloromethane as a solvent.

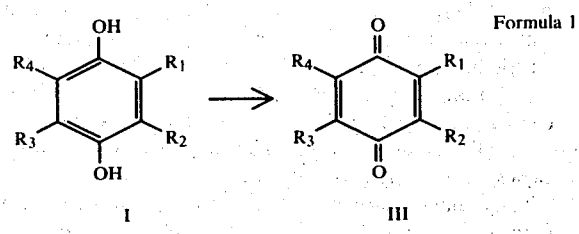

Formula 1

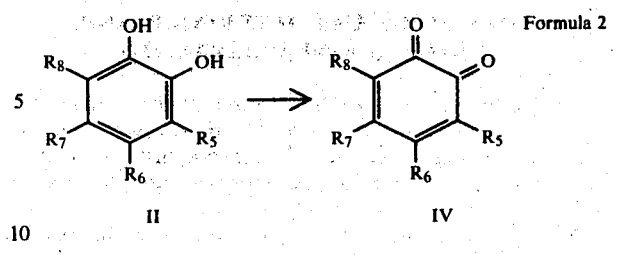

Formula 2

TABLE 2

| | $R_5$ | $R_6$ | $R_7$ | $R_8$ | Solvent | Reaction time (Sec.) | Yield (%) | Melting point (°C.) |
|---|---|---|---|---|---|---|---|---|
| IIa | H | $tC_4H_9$ | H | H | $CH_2Cl_2$ | 10 | IVa 92 | 66–67 |
| IIb | H | $tC_4H_9$ | H | $tC_4H_9$ | $CH_2Cl_2$ | 10 | IVb 91 | 113–114 |

The following are given as the examples embodied of the invention:

EXAMPLE 1

2-t-butyl hydroquinone (Ic) of 3.0 g (18 mmol) are dissolved in 50 ml of chloroform, and wherein 50 ml of 10% hypochloride solution (6.0 g NaOCl, 80 mmol) containing 200 mg (0.59 mmol) of tetra-n-butyl ammonium are added. The solution of hypochloride had been so prepared as to be at pH 8 by using conc. hydrochloric acid, before use.

The mixture reacted is stirred severely for five minutes at room temperature, then, the water and the organic layers of the reacted mixture are separated from each other, and the organic layer is washed with 180 ml of cold water. Thereafter, the organic layer having been washed is dried up by magnesium sulfate anhydrous, and chloroform is removed therefrom at reduced pressure and at 30° C., and the residue is crystallized from 10 ml of hexane. Then, 2-t-butyl benzoquinone (III c) of 2.60 g (15.9 mmol) are obtained. Yield at 88%, m.p. at $54°-55°$ C. [Value in the literature: at $52°-55°$ C. from I. Buben and J. Pospisil, Collect Czech., Chem. Commun., 34, 1991 (1969).]

TABLE 1

| | $R_1$ | $R_2$ | $R_3$ | $R_4$ | Solvent | Reaction time (Sec.) | | Yield (%) | Melting point (°C.) |
|---|---|---|---|---|---|---|---|---|---|
| Ia | H | H | H | H | $CHCl_3$ | 25 | IIIa | 14 | 112–113 |
| Ib | $CH_3$ | H | H | H | " | 10 | IIIb | 72 | 66–67 |
| Ic | $tC_4H_9$ | H | H | H | " | 10 | IIIc | 88 | 54–55 |
| Id | $tC_8H_{17}$ | H | H | H | " | 5 | IIId | 71 | 79–80 |
| Ie | $sC_{18}H_{37}$ | H | H | H | " | 15 | IIIe | 83 | 52–53 |
| If | $C_6H_5$ | H | H | H | " | 10 | IIIf | 82 | 113–114 |
| Ig | $P-CH_3-C_6H_4$ | H | H | H | " | 10 | IIIg | 82 | 138–139 |
| Ih | $tC_4H_9$ | H | $tC_4H_9$ | H | " | 5 | IIIh | 76 | 150–151 |
| Ii | $tC_5H_{11}$ | H | $tC_5H_{11}$ | H | " | 5 | IIIi | 74 | 136–137 |
| Ij | $tC_8H_{17}$ | H | $tC_8H_{17}$ | H | " | 5 | IIIj | 91 | 140–141 |
| Ik | (o-tolyl) | | H | H | " | 15 | IIIk | 70 | 124–125 |
| Il | $CH_3$ | $CH_3$ | $CH_3$ | H | " | 20 | IIIl | 90 | 29–30 |
| Im | $CH_3$ | $CH_3$ | $CH_3$ | $CH_3$ | " | 10 | IIIm | 91 | 109–110 |

EXAMPLE 2

4-t-butyl-o-hydroquinone (II a) of 2.0 g (12 mmol) are dissolved in 40 ml of dichloromethane and the solution is cooled down to −10° C. The solution is gradually added with 15 ml of 10% hypochloride solution having its pH at 9 (1.8 g NaOCl, 24 mmol) and containing 150 ml (0.39 mmol) of tetra-n-butyl ammonium bisulfate. Temperature of the solution is kept between −10° C. and −5° C. and kept stirring for ten minutes, thereafter, the organic layer is separated therefrom and is washed with 100 ml of cold water, and then is dried up by magnesium sulfate anhydrous. At the temperature of 30° C. and reduced pressure, dichloromethane is removed, and the residue is crystallized from 20 ml of hexane. Then, 4-t-butyl-o-benzoquinone (IV a) of 1.81 g (11.1 mmol) are obtained. Yield at 92%, mp at 66°–67° C. [Value in the literature: at 67°–70° C. from I. Buben and J. Pospisil, Collect. Czech. Chem. Commun., 34, 1991 (1969).]

EXAMPLE 3

Investigation has been made of how the pH values of hypochloride solution influence on the yield of the products from the reaction.

The pH values of 10% hypochloride solution are regulated each at 7, 8, 9, 10 and 11 respectively by using conc. hydrochloric acid, and 200 mg of tetra-n-butyl ammonium bisulfate are added into each solution respectively. For the comparison purpose, the equal amount of tetra-n-butyl ammonium bisulfate are added into 10% hypochloride solution (pH 12.6) without regulation of pH which is available on the market.

2-methyl hydroquinone (1b) of 3.0 g (24 mmol) is dissolved in 150 ml of chloroform, wherein 100 ml each of hypochloride solution which have been so prepared as mentioned above are added and each reaction is made in the same way as described in Example 1, and then 2-methyl benzoquinone (IIb) is obtained. Table below shows the yields of isolation corresponding to each case of the investigation:

|  | PH | | | | | |
| --- | --- | --- | --- | --- | --- | --- |
|  | 7 | 8 | 9 | 10 | 11 | 12.6 |
| Yield (%) | 41 | 67 | 72 | 70 | 54 | 23 |

What is claimed is:

1. A method for synthesizing p- or o-benzoquinone derivatives represented by formula III or IV

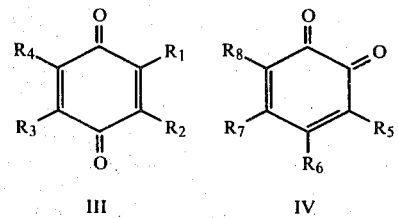

by oxidizing, at a temperature between −20° C. and 35° C., in the presence of a quaternary ammonium salt phase transfer catalyst, with an aqueous hypohalite solution having a pH of from 8 to 10, a p- or o-hydroquinone derivative represented by formula I or II

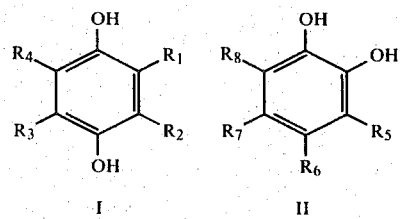

wherein, in formula I, II, III, and IV, $R_1$ through $R_8$, which may be the same or different, represent hydrogen atoms, or alkyl or aryl groups, provided that all the $R_1$, $R_2$, $R_3$ and $R_4$ groups and all the $R_5$, $R_6$, $R_7$ and $R_8$ groups are not hydrogen atoms, and $R_1$ and $R_2$, $R_3$ and $R_4$, $R_5$ and $R_6$, and $R_6$ and $R_7$, respectively, may form a 5 or 6-membered hydrocarbon ring, said temperature being between 0° C. and 35° C. when a compound of formula I is oxidized and between −20° C. and 0° C. when a compound of formula II is oxidized.

2. A method according to claim 1 wherein the hypohalite is hypochlorite or hypobromite.

3. A method according to claim 1 wherein the quaternary ammonium salt phase transfer catalyst is represented by the following formula:

wherein, $R_9$ to $R_{12}$ represent alkyl, aryl, alkylaryl, arylalkyl, and cycloalkyl groups and, by taking two of $R_9$, $R_{10}$, $R_{11}$ or $R_{12}$ together, a five or six-membered heterocyclic ring, and $A^-$ represents a counter anion of a quaternary ammonium cation.

4. A method according to claim 3 wherein the total number of carbon atoms of $R_1$ to $R_4$ is 10 to 30.

5. A method of claim 1 in which a p-hydroquinone is oxidized at a temperature of from 0° C. to 35° C.

6. The method of claim 1 in which an o-hydroquinone is oxidized at a temperature from −20° C. to 0° C.

* * * * *